(12) United States Patent
Stokes et al.

(10) Patent No.: US 8,227,383 B2
(45) Date of Patent: Jul. 24, 2012

(54) LOW INTERFACIAL TENSION SURFACTANTS FOR PETROLEUM APPLICATIONS

(75) Inventors: Kristoffer K. Stokes, Jamaica Plain, MA (US); Michael C. Berg, Somerville, MA (US); David Soane, Chestnut Hill, MA (US); Kevin T. Petersen, Cheshire, CT (US); John H. Dise, Somerville, MA (US); Atul C. Thakrar, Basking Ridge, NJ (US)

(73) Assignee: Soane Energy, LLC, Cambridge, MA (US)

( * ) Notice: Subject to any disclaimer, the term of this patent is extended or adjusted under 35 U.S.C. 154(b) by 214 days.

(21) Appl. No.: 12/481,072

(22) Filed: Jun. 9, 2009

(65) Prior Publication Data
US 2009/0305933 A1    Dec. 10, 2009

Related U.S. Application Data

(60) Provisional application No. 61/060,004, filed on Jun. 9, 2008.

(51) Int. Cl.
C09K 8/60 (2006.01)
C02F 1/68 (2006.01)
C07C 69/76 (2006.01)
C11D 3/20 (2006.01)

(52) U.S. Cl. ............ 507/260; 507/261; 560/3; 210/691; 510/188

(58) Field of Classification Search ............... 510/188; 507/260, 261; 560/3; 210/691
See application file for complete search history.

(56) References Cited

U.S. PATENT DOCUMENTS

| | | | |
|---|---|---|---|
| 3,381,022 | A | 4/1968 | Le Suer |
| 3,542,680 | A | 11/1970 | Le Suer |
| 4,089,803 | A | 5/1978 | Bessler |
| 4,125,382 | A | 11/1978 | O'Brien |
| 4,219,431 | A | 8/1980 | Chibnik |
| 4,240,970 | A * | 12/1980 | Chibnik .................. 549/233 |
| 4,266,610 | A | 5/1981 | Meister |
| 4,300,634 | A | 11/1981 | Clampitt |
| 4,396,530 | A | 8/1983 | Duke |
| 5,268,112 | A | 12/1993 | Hutchins et al. |
| 5,292,843 | A | 3/1994 | Jenkins et al. |
| 7,534,829 | B2 | 5/2009 | Tai et al. |
| 2003/0222026 | A1 | 12/2003 | Carey et al. |
| 2003/0224963 | A1 | 12/2003 | Scheibel |

FOREIGN PATENT DOCUMENTS

WO    2006131541 A1    12/2006
WO    2008033709 A2    3/2008

OTHER PUBLICATIONS

U.S. Appl. No. 12/635,241.
Murillo, M. T., et al., "Bismalonamides (BISMA) as new extractants for Am(III) and Eu(III) from aqueous high level wastes," Radiochimica Acta, 96(4-5): 241-257 (2008).

(Continued)

*Primary Examiner* — Brian P Mruk
(74) *Attorney, Agent, or Firm* — Mahreen Chaudhry Hoda; Carolyn S. Elmore; Elmore Patent Law Group, P.C.

(57) ABSTRACT

The invention relates to a class of novel surfactants that have utility in the recovery and/or extraction of oil.

15 Claims, 3 Drawing Sheets

OTHER PUBLICATIONS

Pereira De Freitas, R., et al., "Synthesis of fullerene building blocks bearing alkyne or azide groups and their subsequent functionalization by the copper mediated Huisgen 1,3-dipolar cycloaddition," Tetrahedron, 64(50): 11409-11419 (2008).

Pierrat, P., et al. "Design and efficient synthesis of fullerene bismalonates as building blocks for metal organic frameworks and organic nanostructures," Synlett, (11): 1706-1710 (2008).

Iehl, J., et al., "Click chemistry with fullerene derivatives," Tetrahedron Letters, 49(25): 4063-4066 (2008).

Rapenne, G., et al. "A new synthon for the incorporation of [60]fullerene in macrocycles," New Journal of Chemistry, 23(12): 1125-1127 (1999).

Nierengarten, J.-F., et al., "Macrocyclization on the Fullerene Core: Direct Regio- and Diastereoselective Multi-Functionalization of [60]Fullerene, and Synthesis of Fullerene-dendrimer Derivatives" Helvetica Chimica Acta, 80(7): 2238-2276 (1997).

Nierengarten, J.-F., "Regio and diastereoselective bisfunctionalization of C60 and enantioselective synthesis of a C60 derivative with a chiral addition pattern," Angew. Chem, Int. Ed. Engl., International Edition in English, 35(18): 2101-2103 (1996).

\* cited by examiner

LOW INTERFACIAL TENSION SURFACTANTS FOR PETROLEUM APPLICATIONS

RELATED APPLICATION

This application claims the benefit of U.S. Provisional Application No. 61/060,004 filed Jun. 9, 2008. The entire teachings of the above application is incorporated herein by reference.

FIELD OF THE APPLICATION

The application relates generally to surfactants useful for petroleum applications.

BACKGROUND

A number of problems in the petroleum industry derive from the viscosity, surface tension, hydrophobicity and density of crude oil. Heavy crude oil in particular, having an API gravity of less than 20 degrees, is difficult to transport due to its viscosity, and is difficult to remove from surfaces to which it has adsorbed, due to its hydrophobicity and immiscibility with water. Extra-heavy crude oil or bitumen, having an API gravity of less than 10 degrees, is heavier than water, so that it can sink to the bottom of a water formation, causing subsurface contamination.

The properties of crude oil contribute to the limitations of oil recovery from traditional oil fields. Conservative estimates suggest that 30% of the technically recoverable oil in U.S. oil fields is inaccessible due to the adsorption of the residual oil to porous geologies. Technologies to unlock the oil in these so-called "dead" wells presently involve the use of hot water injections with expensive surfactants, chemistries that are applied to overcome the hydrophobicity of the adsorbed oil so that it can be mobilized.

The properties of crude oil also contribute to the difficulty of environmental remediation following, for example, an oil spill onto a body of water. The high interfacial tension causes the oil to float on the water and adhere to plants, animals and soil. As the aromatic constituents of the oil evaporate, the heavier residues can sink, contaminating the subsurface structures. Current treatment of spilled oil on water surfaces relies on time-consuming and expensive biological degradation of the oil. Thick, adherent crude oil cause environmental problems in the oil fields as well. Oil deposits attached to vehicles and equipment must be cleansed with jets of hot water and caustics.

The viscosity of heavy crude oil makes the substance difficult and expensive to transport to upgrading facilities. Because of its viscosity, a significant amount of energy is required to pump it through pipelines to a refinery. Furthermore, the viscosity affects the speed at which the heavy crude oil can be pumped, decreasing the overall productivity of an oil field. Exploiting certain oil fields or other oil deposits may be economically unfeasible to develop at present because of the transportation-related costs.

Surfactants have been widely used in the petroleum industry to ameliorate the effects of crude oil's physical properties. Surfactant molecules consist of hydrophobic and hydrophilic parts. Their amphiphilic nature allows them to be adsorbed at an oil/water interface, forming micelles that allow the interfacial tension between oil and water to be reduced.

Surfactants are sometimes used for desalting of crude oil. Desalting refers to the process of removing salts from oil, making the oil more suitable for further refining. The salts are typically dissolved in water that is associated with oil, so the removal of water has multiple benefits. The presence of water reduces the energy content of oil, and it carries salts that can harm catalyst performance or cause corrosion. Ethoxylated nonylphenols have been used for desalting of crude oil, but these compounds pose hazards to the environment.

Furthermore, surfactant technologies for the aforesaid petroleum applications typically are expensive or must be used at high concentrations. Additionally, demulsification can prove to be difficult, as these surfactants are designed for emulsifying purposes. Demulsification typically requires added materials and steps to break up the emulsion, which increases the effective cost of use. Furthermore, the salts present in nature can inactivate many surfactant technologies. In addition, other surfactant technologies for petroleum applications are tailored only to oils of a limited composition.

The development of a technology that can provide emulsion and favorable transport properties while maintaining the ability to demulsify on demand, all under variable conditions of salinity, remains unmet in the art. Such a technology would have wide reaching impact across the oilfield chemical sector in applications such as those mentioned above, particularly if the material could be inexpensively produced and could be applied to a variety of oil types.

SUMMARY

The invention relates to the discovery that novel surfactants have good to excellent properties in recovering or extracting oil, such as fossil fuels. Accordingly, in some embodiments, the invention relates to a compound having the formula I:

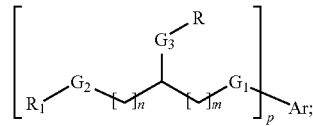

wherein Ar is a substituted or unsubstituted aryl, aralkyl (e.g., benzyl) or heteroaryl group; in some embodiments, Ar is a substituted or unsubstituted aryl, heteroaryl group, preferably a substituted or unsubstituted phenyl group;

p is 1 or 2, preferably 2;

m and n are independently 0, 1, 2, 3, 4, or 5, preferably 1;

each of $G_1$ and $G_2$ are independently absent, O, S, $NR_2$, (CO)O, O(CO), CO, $CONR_2$, or $NR_2CO$; preferably each $G_1$ and $G_2$ are independently O or C(O)O;

each $R_2$ is independently H or a lower alkyl; in some embodiments, the lower alkyl is a C1 to C5 alkyl;

each $G_3$ is independently absent, $(CH_2)_q$ or $G_1$;

q is 1, 2, 3, 4 or 5;

R is a hydrophilic group; preferably the hydrophilic group is COOH, or a hydrophilic polymer, such as a polyethylene glycol or a polypropyleneoxide;

$R_1$ is a saturated or unsaturated hydrophobic aliphatic group; in some embodiments, $R_1$ is $C_5$ to $C_{18}$ alkyl, alkenyl or alkadienyl, preferably a straight chain $C_5$ to $C_{18}$ alkyl;

wherein, when p is 1, Ar is substituted by one or more of $OR_2$, $SR_2$ and $N(R_2)_2$;

preferably, when p is 1 Ar is substituted by OH, SH or $NH_2$.

In one preferred embodiment, $G_1$ is C(O)O, $G_2$ is absent and n is 0. Alternatively, where $G_1$ is O, $G_2$ is not absent, and is preferably O or (CO)O.

A particularly preferred surfactant is a compound having the formula (II):

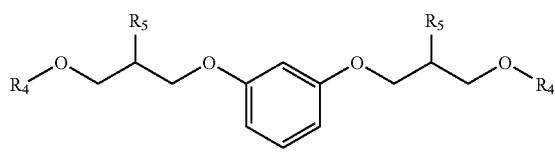

wherein $R_5$ is a hydrophilic group; and
$R_4$ is a saturated or unsaturated hydrophobic aliphatic group.

The invention further relates to a compound having formula III:

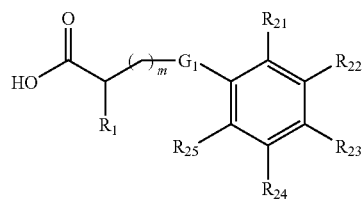

wherein $G_1$ is selected from the group consisting of S, $NR_2$, (CO)O, O(CO), CO, $CONR_2$, and $NR_2CO$; preferably G1 is C(O)O;
each $R_2$ is independently H or a lower alkyl;
wherein, $R_{21}$, $R_{22}$, $R_{23}$, $R_{24}$, and $R_{25}$ are each independently, H, OH, halogen, $C_1$-$C_5$ alkyl, $C_1$-$C_5$ alkoxy, a $C_3$-$C_7$-cycloalkyl group, a phenyl group optionally substituted by hydroxyl, halogen, lower alkyl or lower alkoxy, or Fragment I having the formula shown below:

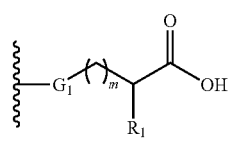

wherein $R_1$, m and $G_1$ are as defined above;
wherein at least one of $R_{21}$, $R_{22}$, $R_{23}$, $R_{24}$, and $R_{25}$ is Fragment I or OH;
or a salt thereof.

A particularly preferred surfactant is a compound having the formula IV:

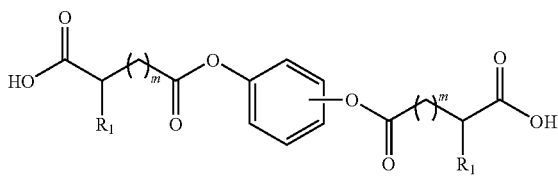

wherein m and $R_1$ are as defined above.

Preferred compounds of formula IV are compounds wherein m is 1 and $R_1$ is a straight chain $C_5$ to $C_{18}$ alkyl.

The invention further relates to a method for extracting oil from an oil mixture comprising:
(a) adding a compound of Formula I to an oil mixture, and
(b) collecting the oil.

The oil mixture may comprise oil sands, waterborne oil slicks or oil deposits. Further, the method can comprise the additional steps of adding water or transporting the mixture via a pipeline. In another embodiment, the compounds of the invention can be used in methods of degreasing machinery, such as those used in oil or bitumen production.

DETAILED DESCRIPTION

General Formulations

Figure 1:
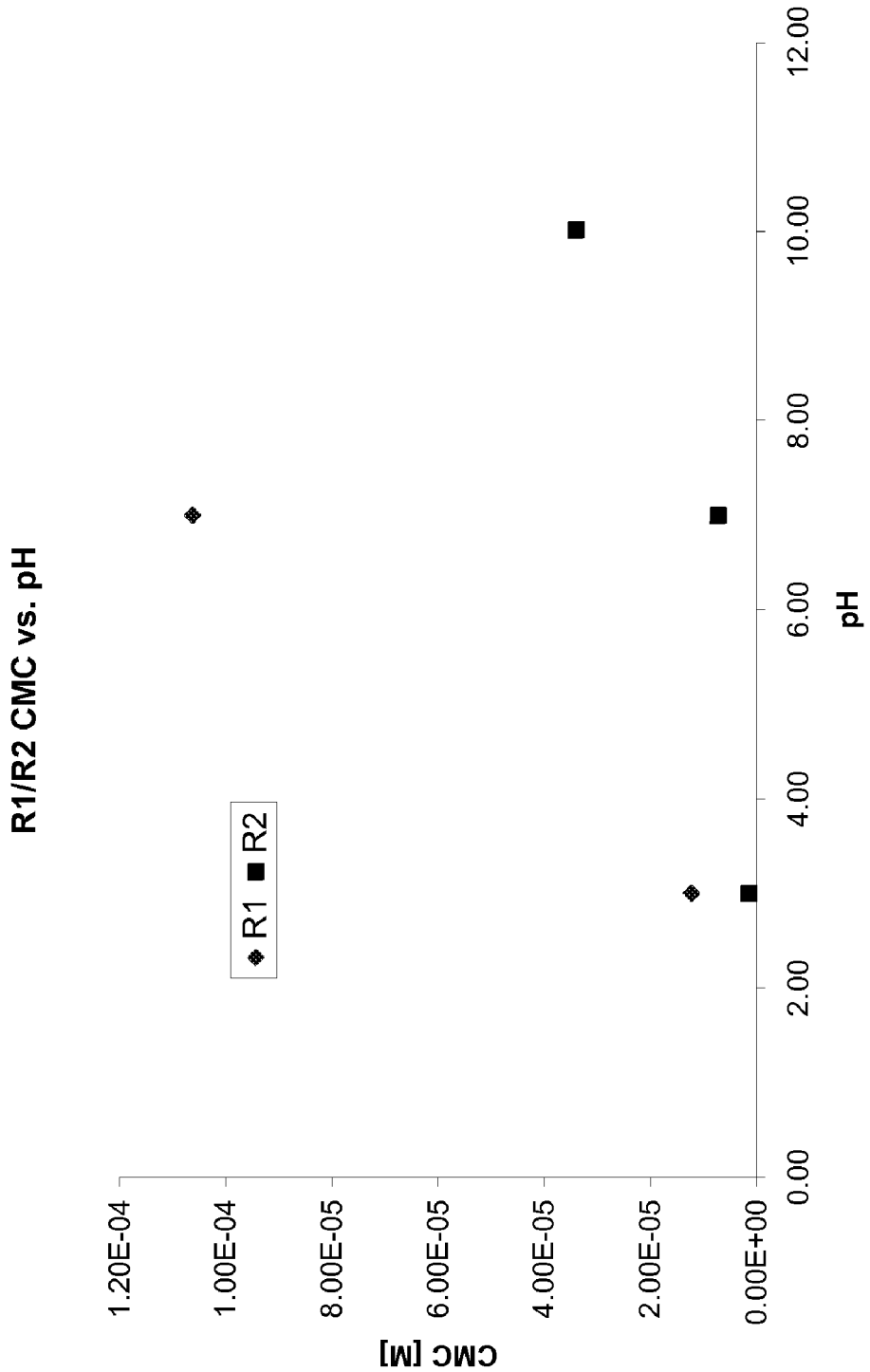
FIG. 1 illustrates examples of critical micelle concentration of compounds of formulas shown below, termed R1 and R2, on the graphs below.

Disclosed herein are compositions, systems and methods related to ultra-low interfacial tension ("IFT") surfactants for applications in the petroleum industry. In certain embodiments, the present disclosure is based on the discovery that certain resorcinol-based ester surfactants are highly effective surfactants for petroleum applications, and can be used as additives in petroleum processing, oil sands extraction and processing, environmental remediation, enhanced oil recovery, and the like. In one embodiment, compositions of particular use in these systems and methods can include at least one compound of the formula (V):

Formula V

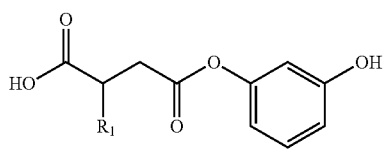

Wherein $R_1$ is a hydrophobic group as defined above.

In alternate embodiments, compositions of particular use in these systems and methods can include at least one compound of formula (VI):

Formula VI

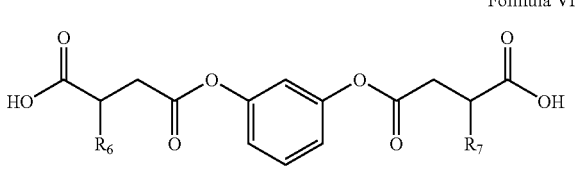

In one embodiment, compositions of particular use in these systems and methods can include at least one compound of the formula (VII):

Formula VII

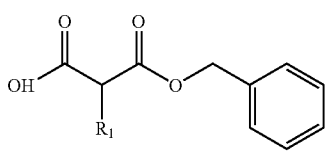

wherein $R_6$ and $R_7$ are each independently a hydrophobic group and $R_1$ is as defined above.

The compounds described herein can be used as surfactants. The inventive surfactant compounds comprise an aromatic core with pendant aliphatic hydrophobic and hydrophilic portions. As will be understood by one of skill in the art the hydrophobic portion of the surfactant compound can comprise one or more hydrophobic groups or substituents. Similarly, the hydrophilic portion of the inventive compounds can comprise one or more hydrophilic groups or substituents. Attached aliphatic hydrophobic portions or groups can consist of linear or branched, saturated or unsaturated, substituted or unsubstituted higher alkyls. For example, the hydrophobic group can be derived from alkanes with or without internal or terminal alkenes. In some embodiments, the higher alkyl comprises at least five carbon atoms. In other embodiments, the higher alkyl is a $C_5$ to $C_{18}$ alkyl, alkenyl or alkadienyl. Hydrophilic portions or groups can be an ionizable groups, including, for example, amines and carboxylic acids. Hydrophilic groups also include hydrophilic polymers, including, but not limited to, polyalkylamine, poly(ethylene glycol) or poly(propylene glycol). Nonionic hydrophilic materials such as polyalkylamine, poly(ethylene glycol) or poly(propylene glycol) can be used to increase hydrophilicity or aid stability in salt solutions.

In some embodiments, the aliphatic groups include saturated or unsaturated carbon chains, preferably between five and eighteen units in length, or hydrogen. The carbon chains can optionally be unsaturated and, when present, reside anywhere along the carbon chain.

The aromatic core can be carbocyclic or heterocyclic, monocyclic or polycyclic, substituted or unsubtstituted. Preferred aryl groups can be derived from resorcinol, phenol, creosol, benzyl alcohol, naphthalene, anthracene, pyrene, tetrahydronaphthyl, indanyl, idenyl and the like. Heteroaromatic structures such as thiophene, selenophene, silole, pyrrole, pyridine, furan, imidazole, indole, pyrazinyl, pyrimidinyl, pyrazolyl, imidazolyl, thiazolyl, oxazolyl, isooxazolyl, thiadiazolyl, oxadiazolyl, furanyl, quinolinyl, isoquinolinyl, benzimidazolyl, benzooxazolyl, quinoxalinyl, and the like can also be used as the aromatic core. The term "substituted" refers to substitution by independent replacement of one or more of the hydrogen atoms thereon with substituents including, but not limited to, —OH, —$NH_2$, —NH—$C_1$-$C_{12}$-alkyl, —O—$C_1$-$C_{12}$-alkyl, —SH, and —S—$C_1$-$C_{12}$-alkyl.

In certain aspects of the invention, the hydrophilic portion of compounds of the invention is one or more ionizable carboxylic acid groups, which groups make up the totality of the hydrophilic portion. By themselves, the carboxylic acid portions are not enough to effectively stabilize emulsions formed by the mixture of a waterborne suspension of the disclosed surfactant compounds. Addition of a small amount of base (greater than pH 8) is sufficient to ionize, leaving a more active, emulsion-forming material. The emulsion can later be destabilized by adding acid to the material, removing the charge stabilization and splitting the two incompatible phases.

Changing pH is one method to enabling and disabling the surfactant behavior; however, compounds of formula (I) and formula (III) are typically unstable hydrolytically. For example, in certain embodiments, exposure to base for prolonged periods of time will degrade the compounds of formula (I) and formula (III) to resorcinol and alkylated succinic acid. The decomposition byproducts have little to no surfactant behavior, and thus can be utilized as another means to destabilize the formed emulsion. The disintegration follows a predictable profile which can be exploited for tunable, time-based demulsion.

This behavior has utility for petroleum-related applications. If one knows, for example, the residence time of oil in a pipeline, the amount of base can be precisely calculated and added to cause decomposition begin in the pipeline and separation to occur immediately after the emulsion reaches its destination. This has the benefit of decreasing residence time in a storage facility while the emulsion breaks.

Applications

Environmental Remediation

By taking advantage of the low IFT behavior of the surfactant families disclosed herein, such surfactants may be suitable for applications where undesired petroleum products pose an environmental problem. Oil cleanup using surfactants may be required for two different types of contamination. First, as an oil slick dispersant, the surfactant family can be used on waterborne slicks, acting as a dispersing agent. It will act to disperse the oil into the water body itself and encourage biodegradation through natural decomposition means. Additionally, a solution of surfactant can be used to remove physisorbed crude or refined oils from inorganic rocks, sand, or other substrates as an emulsion.

Oil Sands Extraction

Oil sands comprise heavy petroleum products coating sand and clay, an assemblage that is similar to certain artificial composites that are formed during a man-made oil spill, as described above. The systems and methods described herein may be useful for extracting bitumen from the other components of the tar sands material. Currently, mined oil sands are extracted using hot water, a process that causes the less dense bitumen to flow off the sand and float to the surface of a settling tank. This so-called "primary froth" is contaminated with various materials derived from the mined products (solid particles, clay, and sand). Current froth treatment utilizes naphtha, a valuable fraction of purified petroleum, to dilute the bitumen and decrease the viscosity to the point of flowability. This allows solids and water to be removed by settling and centrifugation methods. By using an aqueous solution of surfactant as the dilution medium instead of naphtha, the latter solvent can be replaced with water and surfactant, thus decreasing the cost of purifying the froth. Additionally, when the surfactant-diluted bitumen is recovered from the water, the hydrophilic portions associated with the froth (clay, water, salts) will preferentially partition to the water phase and be separable from the bitumen.

Use of surfactants in accordance with these systems and methods may further be applied to other aspects of the extraction process, for example in the oil sands strip mining or in-situ operations, where the ability to emulsify the petroleum component of the oil sands ore may enhance the efficiency or economy of separating the bitumen from the insoluble byproducts.

Oil Field Transport Emulsions

Transporting petroleum precursors for further processing is a necessary, though expensive, part of obtaining usable crude oil. When petroleum is obtained as a heavy crude, it needs to be transported to an upgrading facility for conversion to useful petroleum products. Typically, pipeline transport is the most economical means to accomplish this. When oil sands are used as precursors in the production of synthetic crude oil, they are transported for further processing after extraction and froth treatment through pipelines as a naphtha-diluted bitumen so that they can undergo further upgrading processes, including cracking and coking, amongst other standard refining operations. For these types of applications in the petroleum and tar sands industries, the heavy oil or oil precursor materials (respectively) may be transported through pipelines as oil-in-water mixtures or emulsions. It is understood that more viscous matter being sent through pipelines has a greater resistance to flow and consequently requires more energy to move an equivalent distance. Hence, decreasing the viscosity of the flowable matter decreases the amount of pumping energy required, and potentially improves the transit time and the productivity of the overall process. Mixing water with crude oil or bitumen can decrease the viscosity of these latter substances towards the viscosity of water, but only if a water-continuous emulsion is created. The described low IFT surfactants can compatibilize oil and water into an emulsion that can be pumped with greatly decreased energy requirements and/or increase the throughput of crude oil or oil precursors to their destinations.

Auxiliary Petroleum Applications

There also exist many other opportunities in the oilfield chemical sector for degreasing applications, as can be accomplished with the systems and methods disclosed herein. Periodically, machinery used in oil and bitumen production must be cleaned for maintenance and performance reasons. With petroleum production heading towards heavier crude reserves, the need for an effective degreaser becomes even more acute: exposure to heavier crude oils results in thicker, more adherent oil residues that must be removed during the cleaning/degreasing processes. The described low IFT surfactants can be an active ingredient in an industrial degreasing formulation for these purposes.

Enhanced Oil Recovery (EOR)

Tertiary oil recovery, also known as "enhanced" or "improved" oil recovery, makes use of low IFT polymers to produce oil from wells that have stopped producing of their own accord. Injection of a low IFT surfactant into one of these less productive wells can stimulate production from the residual oil left adhered to the surface of porous rocks. Compounds produced according to these systems and methods are useful as low IFT surfactants for EOR. Due to the temperatures and residence time underground, certain esters made in accordance with formula (I) or formula (II) may be too unstable for these applications. In addition, the resident acid groups on the compound of formula (II) are highly sensitive to saline commonly found in well formations.

The compound of formula (III) may be particularly suitable for EOR applications:

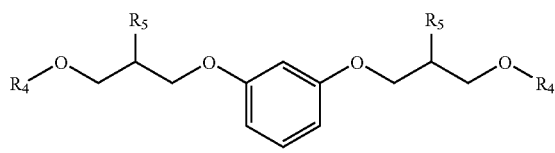

$R_4$ and $R_5$ are as defined above.

In some embodiments, $R_4$ can include a linear or branched carbon chain consisting of five to eighteen carbon atoms. Advantageously, substituent R4 can be a saturated or unsaturated carbon chain consisting of five to eighteen carbon atoms.

In some embodiments, $R_5$ can include water soluble oligomers such as poly(ethylene glycol) or poly(propylene oxide). By using a small poly(ethylene glycol) as the hydrophilic portion the substituent $R_5$, and all ether connectivity, the molecule of formula (II) may desirably withstand the temperature and salinities found underground for the requisite time period.

Desalting

Desalting refers to the process of removing salts from oil, making the oil more suitable for further refining. Salts, including magnesium chloride, sodium chloride and calcium chloride can be found in crude oil. If allowed to remain in the crude oil during the refinery operation, the salts can dissociate and the chloride ion can ionize to form hydrochloric acid, which, along with various organic acids found in crude oil, contributes to corrosion in refinery equipment. In addition, other metal salts (e.g., potassium, nickel, vanadium, copper, iron and zinc) can be found in the crude oil, also contributing to fouling of the equipment and end-product degradation. Crude oil also contains emulsified water, which contains dissolved salts.

Desalting crude oil takes advantage of the fact that the salts dissolve in a water phase, which is separable from the oil phase. Crude oil naturally contains water in emulsion, as mentioned above. For certain techniques of desalting, additional water may be added to the oil (e.g., in an amount between 5-10% by volume of crude) so that the impurities can further dissolve in the water. The water-in-oil emulsion can be broken with the assistance of emulsion-breaking chemicals and/or by exposing the emulsion to an electrical field that polarizes the water phase, so that the water phase bearing the impurities separates from the petroleum phase. Ethoxylated nonylphenols are a class of nonionic surfactants that have been used for desalting crude oil according to these principles.

The surfactant families disclosed herein can facilitate the demulsification of the water-in-oil emulsion, so that the oil phase separates from the water phase, with the water phase carrying the soluble impurities (i.e., the salts). In embodiments, the hydrophilic portion of the surfactant compound can include one or more ionizable carboxylic acid groups that can be ionized at a basic pH (e.g., >8) to produce an emulsion-sustaining material. To destabilize the emulsion, acid may be added, removing the charge stabilization and allowing the two phases to segregate from each other.

EXAMPLES

Example 1

Synthesis of Compounds of Formula (I)

Compounds having the structure of formula (I) may be synthesized as follows:

A 300 ml bomb is charged with resorcinol (5 g, 48 mmol) and Eka SA 210 brand alkylated succinic anhydride (100% C18 chain, 16.8 g., 48 mmol). To this, acetone (150 ml) is added, the vessel is sealed and heated to 80° C. for 16 hours. After the reaction is complete, acetone is removed in vacuo and the remaining amber oil is collected in quantitative yield. The scheme below illustrates this Synthesis I.

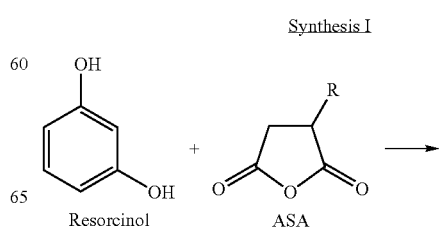

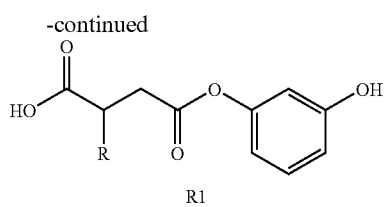

R1

Example 2

Synthesis of Compounds of Formula (II)

Compounds having the structure of formula (II) may be synthesized as follows:

A 300 ml bomb is charged with resorcinol (5 g, 48 mmol) and Eka SA 210 brand alkylated succinic anhydride (100% $C_{18}$ chain, 33.7 g, 96 mmol). To this, acetone (150 ml) is added, the vessel sealed, and heated to 80° C. for 16 hours. After the reaction is completed, acetone is removed in vacuo and the remaining amber oil is collected in quantitative yield. The scheme below illustrates this Synthesis II.

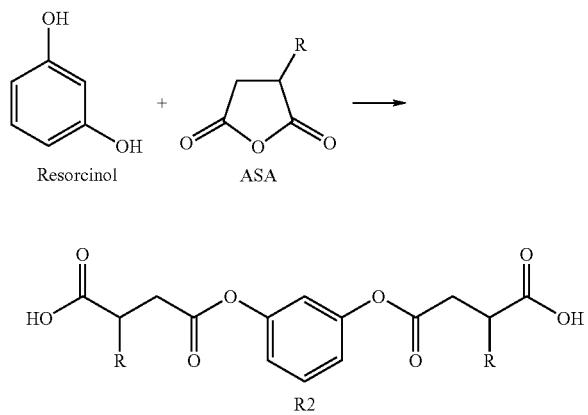

R2

Example 3

Proposed Synthesis of Compounds of Formula (II)

Compounds having the structure of formula (II) may be synthesized as follows:

A 300 ml bomb is charged with resorcinol (5 g, 48 mmol) and glycidyl hexadecyl ether (28.6 g, 96 mmol). To this, acetone (150 ml) is added, the vessel sealed, and the mixture heated to 80° C. for 16 hours. After this first addition, the material is isolated and dried under vacuum. The alcohol moieties created by the epoxide ring opening is used as initiators in an ethylene oxide polymerization to create a hydrophilic portions on the surfactant, under standard ethylene oxide polymerization conditions. The scheme below illustrates this Synthesis III:

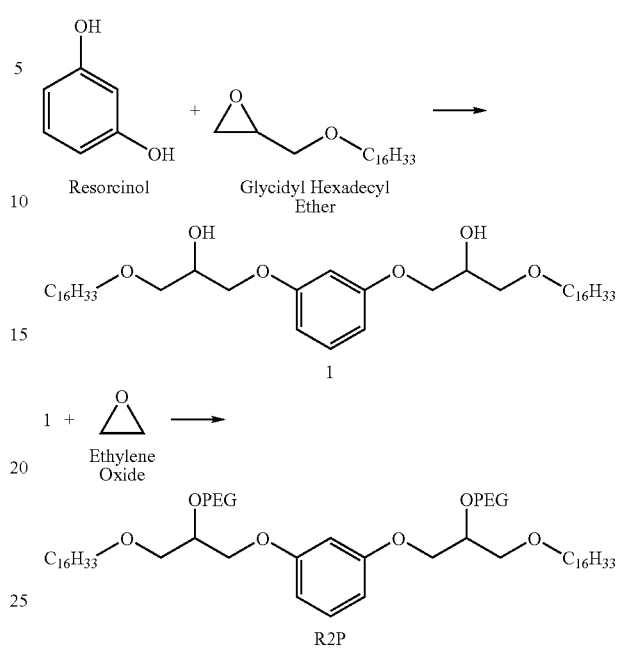

Example 4

Proposed Synthesis of Compounds of Formula (II)

Compounds having the structure of formula (III) may be synthesized as follows:

A 300 ml bomb is charged with resorcinol (5 g, 48 mmol) and glycidyl hexadecyl ether (14.3 g, 48 mmol). To this, acetone (150 ml) is added, the vessel sealed, and the mixture heated to 80° C. for 16 hours. After this first addition, the material is isolated and dried under vacuum. The alcohol moieties created by the epoxide ring opening is used in the next reaction to add hydrophilic portions to the molecule. Compound 1 is dissolved in acetone and heated to 80° C. to complete the reaction without the need for an ethylene oxide polymerization. The scheme below illustrates this Synthesis IV.

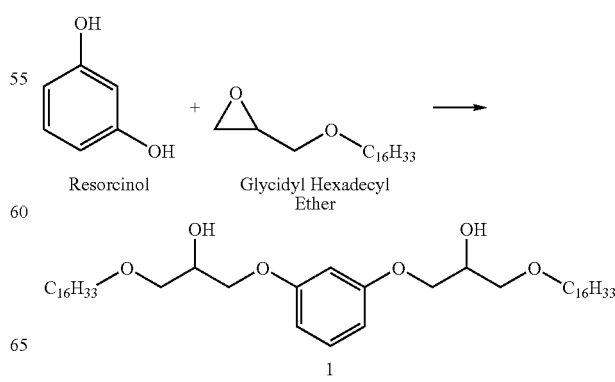

-continued

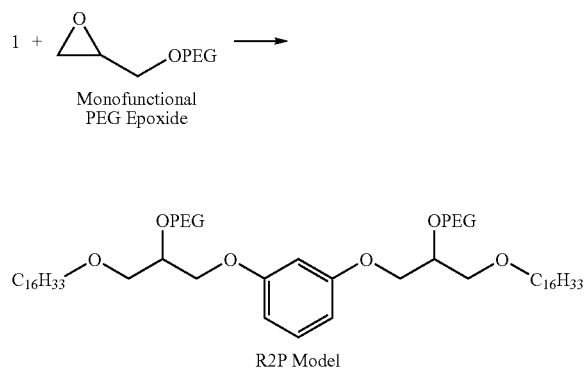

Monofunctional PEG Epoxide

R2P Model

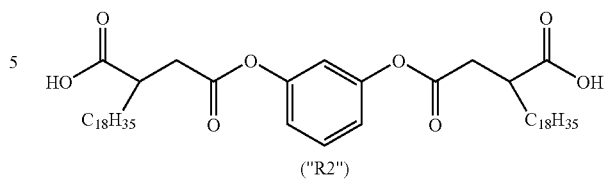

("R2")

Example 6

Emulsion Stability for Oil Flow Behavior

Figure 3:
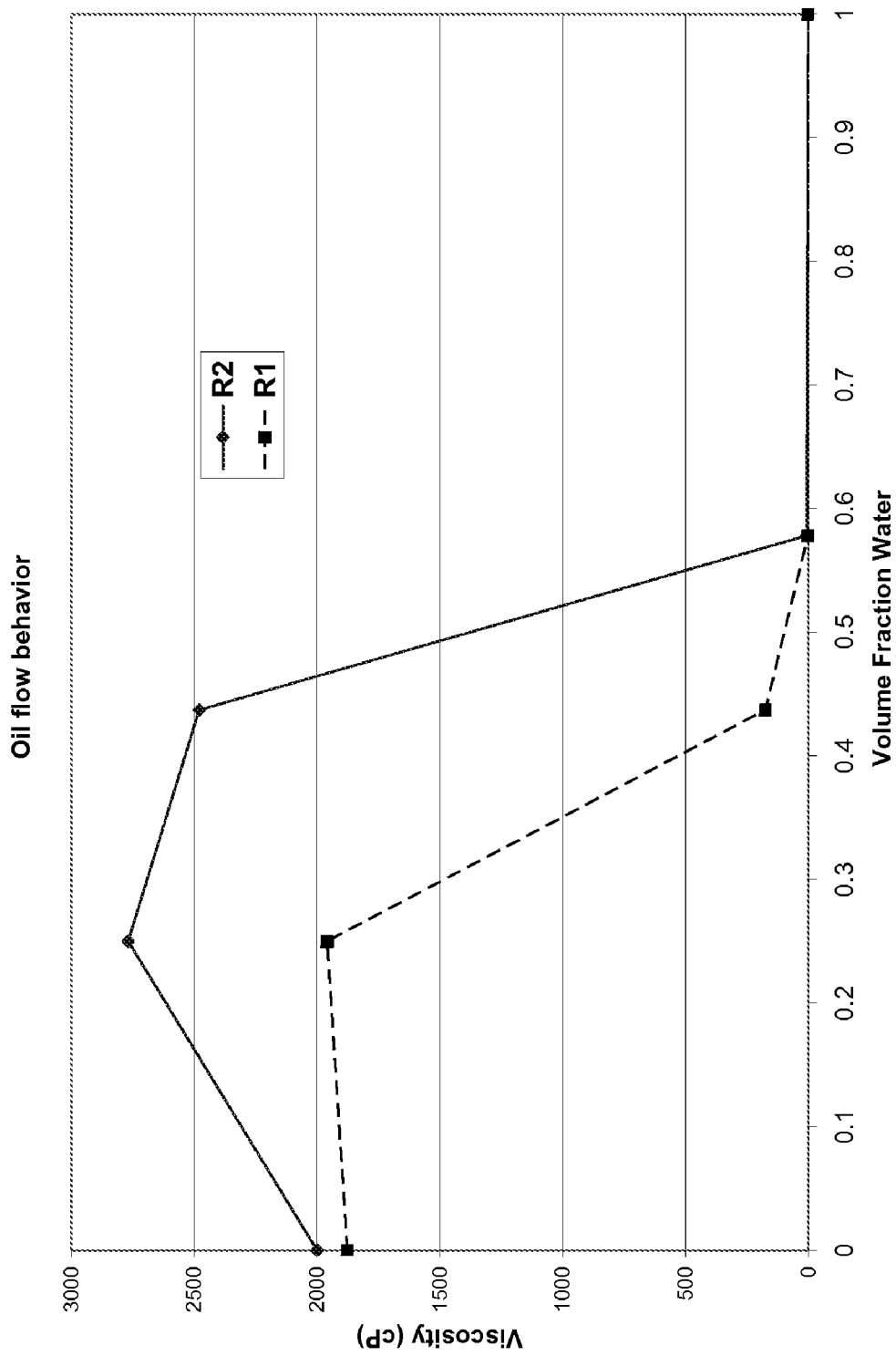
FIG. 3 compares the capabilities of the R1 and R2 surfactants in emulsifying and transporting heavy crude oils, measuring the viscosity of diluted bitumen.

In order to test the capabilities of the surfactants in emulsifying and transporting heavy crude oils, the viscosity was measured with various additions of surfactant solution on a Brookfield viscometer at 22° C. Compounds of formula (VI), designated as R1, and compounds of formula (VII), designated as R2, were tested. Using a LV3 type spindle at 40 RPM, the diluted bitumen (residual toluene mixed with bitumen) demonstrated a viscosity of approximately 2000 cP. This diluted bitumen was then mixed with multiple ratios of a 1 wt % solution of R1 or R2 in deionized water with the pH adjusted to 9 for emulsion activity. FIG. 3 illustrates the results of these tests, showing the viscosity of diluted bitumen as a function of surfactant solution addition.

FIG. 3 demonstrates that incorporation of an aqueous solution of surfactant can dramatically decrease the viscosity of diluted bitumen. As shown in FIG. 3, the addition of more than 50 vol % of a dilute aqueous solution of R1 or R2 decreases the bitumen viscosity by nearly one thousand times. The energy savings of such a system are significant, but the concomitant increase in flowrate enables much higher throughput and residence time in a pipeline.

Example 5

Critical Micelle Concentration

Critical micelle concentration (CMC) is an important metric with surfactant systems. It is defined as the minimum surfactant concentration that will form micelles. Below this amount, the molecules exist only in a non-aggregated form. Additionally, this number also represents the constant concentration of monomeric molecules in solution. Effectively, it describes a lower limit to usage and is a good first approximation to formulation content.

A series of aqueous surfactant dilutions were prepared in deionized water with concentrations between 20 μM and 200 mM. The water surface tension at 22° C. was measured on a KSV 702 tensiometer using the Du Nouy ring method. Measured surface tensions were plotted against concentration and linear regression analysis was used to find the inflection point denoting the critical micelle concentration (CMC) of the surfactant. For testing at higher or lower pH conditions, 0.1 M buffer solutions were used. Citric acid buffer was used to stabilize pH 3 while sodium bicarbonate was used for a pH 10 buffer.

FIG. 1 illustrates examples of critical micelle concentration of a compound of formula shown below, termed R1 on the graphs below. R1 is a species of a compound of formula (I). FIG. 1 also illustrates examples of critical micelle concentration of a compound of formula shown below, termed R2 on the graphs below.

EQUIVALENTS

While specific embodiments of the subject invention have been discussed, the above specification is illustrative and not restrictive. Many variations of the invention will become apparent to those skilled in the art upon review of this specification. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth herein are approximations that can vary depending upon the desired properties sought to be obtained by the present invention.

The invention claimed is:

1. A compound having the formula:

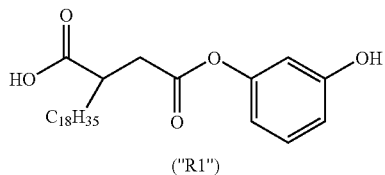

("R1")

Figure 2:
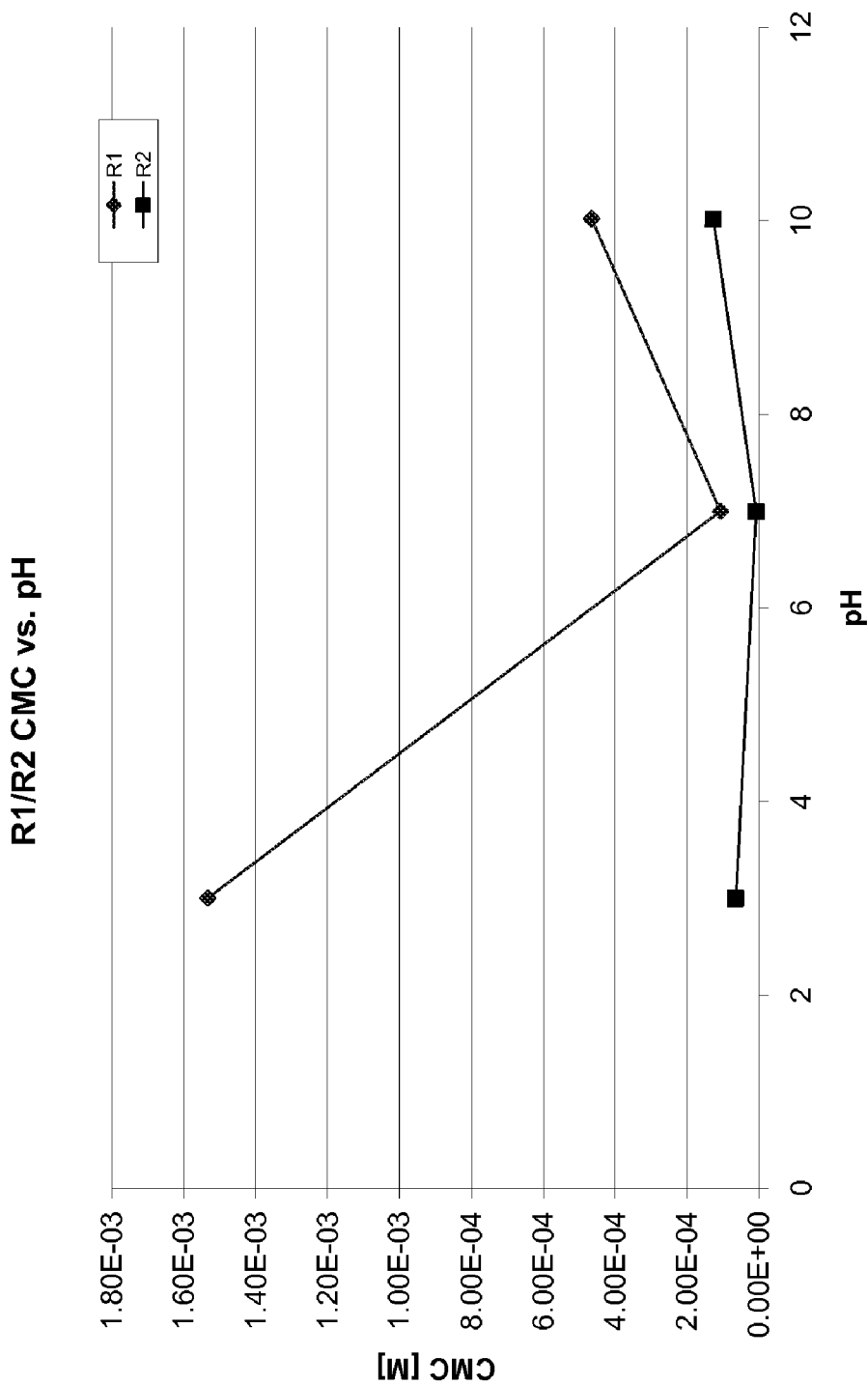
FIG. 2 shows a plot of CMC as a function of pH for two molecules, R1 and R2.

FIG. 2 shows a plot of CMC as a function of pH for two molecules, R1 (shown above) and a compound of formula (V), termed R2 in the graphs below. R2 is a species of a compound of formula (II).

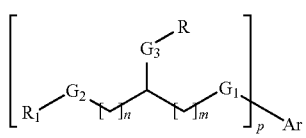

wherein Ar is a substituted or unsubstituted arylalkyl group;

p is 1 or 2;

m and n are independently 0, 1, 2, 3, 4, or 5;

each $G_1$ is C(O)O or OC(O) and each $G_2$ is absent;

each $R_2$ is independently H or a lower alkyl;
each $G_3$ is $(CH_2)_q$;
q is 1, 2, 3, 4 or 5;
R is a hydrophilic group;
$R_1$ is a saturated or unsaturated hydrophobic aliphatic group selected from the group consisting of $C_5$ to $C_{18}$ alkyl, $C_5$ to $C_{18}$ alkenyl and $C_5$ to $C_{18}$ alkadienyl;
wherein when p is 1, Ar is substituted by OH, SH or $NH_2$; and
wherein when at least one $G_2$ is absent, $G_1$ is other than O.

2. The compound of claim 1 wherein p is 2.

3. The compound of claim 2 wherein each R is independently C(O)OH or a hydrophilic polymer.

4. The compound of claim 3 wherein each R is independently a polyethylene glycol or a polypropyleneoxide.

5. The compound of claim 2 wherein each $R_1$ is independently $C_5$ to $C_{18}$ alkyl.

6. The compound of claim 5 wherein each $R_1$ is a straight chain $C_5$ to $C_{18}$ alkyl.

7. A method for extracting oil from an oil mixture comprising:
    (a) adding a compound of claim 1 to an oil mixture, and
    (b) collecting the oil.

8. The method of claim 7 wherein the oil mixture comprises oil sands, wherein said method further comprises adding water to the mixture.

9. The method of claim 7 wherein the oil mixture is a waterborne oil slick.

10. The method of claim 7 wherein the oil mixture formed by step (a) is transported via a pipeline.

11. The method of claim 7 wherein step (a) occurs in an oil well to enhance oil recovery.

12. A method of degreasing machinery used in oil or bitumen production comprising cleaning the machinery with a composition comprising a compound of claim 1.

13. A method of removing water and associated salts from oil, comprising:
    (a) contacting the oil with a compound of claim 1, and
    (b) separating the water from the oil.

14. The compound of claim 1, wherein Ar is substituted or unsubstituted benzyl.

15. The compound of claim 1, wherein each R is independently an ionizable group selected from the group consisting of a carboxylic acid group and an amine group.

* * * * *